United States Patent [19]
Borden et al.

[11] Patent Number: 5,942,611
[45] Date of Patent: Aug. 24, 1999

[54] PROCESS FOR NATAMYCIN RECOVERY

[75] Inventors: George Wayne Borden, Cape Haze, Fla.; John Michael Maher, East Lyme; Constantine Sklavounos, Waterford, both of Conn.

[73] Assignee: Cultor Ltd., Finland

[21] Appl. No.: 08/696,841

[22] PCT Filed: Jan. 19, 1995

[86] PCT No.: PCT/IB95/00040

§ 371 Date: Aug. 28, 1996

§ 102(e) Date: Aug. 28, 1996

[87] PCT Pub. No.: WO95/27073

PCT Pub. Date: Oct. 12, 1995

[51] Int. Cl.⁶ ........................................................ C07H 1/00

[52] U.S. Cl. ............................ 536/127; 536/6.5; 536/16.9

[58] Field of Search ............................ 536/6.5, 127, 16.9

[56] References Cited

U.S. PATENT DOCUMENTS

| | | | |
|---|---|---|---|
| 3,378,441 | 4/1968 | Bridge | 536/127 |
| 3,892,850 | 7/1975 | Struyk et al. | 435/76 |
| 4,568,740 | 2/1986 | Oppici et al. | 536/7.5 |
| 5,231,014 | 7/1993 | Eisenschink et al. | 435/76 |

FOREIGN PATENT DOCUMENTS

| | | |
|---|---|---|
| 846933 | 9/1960 | United Kingdom . |
| 2106498 | 4/1983 | United Kingdom . |
| 9210580 | 6/1992 | WIPO . |
| 9507998 | 3/1995 | WIPO . |

*Primary Examiner*—Elli Peselev

[57] ABSTRACT

A new process for recovering high purity natamycin from fermentation broth containing natamycin comprises the steps of adjusting the pH of the broth to above about 10 and adding an amount of a water-miscible solvent, such as isopropanol, sufficient to dissolve the natamycin in the broth, followed by removing insoluble solids from the pH-adjusted broth, followed by lowering the pH of the broth to a level sufficient to precipitate the natamycin, and removing the natamycin from the broth.

12 Claims, No Drawings

PROCESS FOR NATAMYCIN RECOVERY

BACKGROUND OF THE INVENTION

Natamycin, also known as pimaricin, was first isolated in 1955 from the fermentation broth of a culture of *Streptomyces natalensis* obtained from soil taken near the town of Pietermaritzburg In Natal, South Africa. (A. P. Struyk et al, *Antibiotics Annual*, 878 (1957–1958)). Pimaricin, designated natamycin by the WHO, is produced either from *Streptomyces natalensis* or *Streptomyces gilvosporeus*.

Early patents describe recovery processes requiring multiple purification steps and involving relatively expensive unit operations. British patent GB 846,933 discloses an adsorption/elution recovery of natamycin from fermentation broth using water miscible polar solvents such as methanol, butanol and acetone. U.S. Pat. No. 3,892,850 discloses recovery from fermentation broth by extraction into an organic solvent having limited water miscibility, followed by recovery from the solvent. U.S. Pat. No. 3,378,441 claims recovery of natamycin by salting it out of fermentation broth followed by solvent dissolution and evaporative precipitation. A later patent, GB 2,106,498, describes vacuum concentration or butanol extraction of filtered fermentation broth to obtain a raw antifungal complex from which natamycin can be isolated. WO 92/10580 discloses solubilization of natamycin with methanol at low pH, followed by removal of broth solids. Under these conditions, natamycin is susceptible to acid degradation, with potential for depressed recovery yield and reduced product purity. Thus, the prior art does not teach an efficient method for recovery of high quality natamycin.

SUMMARY OF THE INVENTION

The present invention concerns a new, simple and efficient process to recover high quality natamycin from fermentation broth using a substantially water-miscible solvent at alkaline pH. Specifically, natamycin is recovered from the fermentation broth via a process comprising the steps:

a) adjusting the pH of the broth to greater than about 10 and adding an amount of a substantially water-miscible solvent sufficient to dissolve the natamycin in the broth;

b) removing insoluble solids from the pH-adjusted broth;

c) lowering the pH of said broth to a level sufficient to precipitate the natamycin from the broth; and d) removing the natamycin from the broth.

In its preferred embodiment, the pH of the broth is adjusted to between 10 and 11 in step a) and to between 5.5 and 7.5 in step c). Any of several methods may be used in steps b) and d), for example, centrifugation, depth filtration and crossflow filtration, with a preferred method being crossflow filtration. It is preferred that, prior to the recovery process, the fermentation broth is concentrated, for example, to a concentration of from 10 to 50% solids, on a weight/volume basis. For greater stability of the natamycin during the recovery process, an antioxidant such as BHA, BHT, ascorbic acid or sodium erythorbate can be added.

DETAILED DESCRIPTION OF THE INVENTION

The production of natamycin by fermentation is well known. The aforementioned British patent, GB 846,933, is representative and discloses the production of natamycin via fermentation using *Streptomyces gilvosporeus*. The fermentation method itself is not critical to the present invention.

Fermentation broth containing natamycin may be concentrated, if desired, through any suitable method such as evaporation, depth filtration, crossflow filtration or centrifugation, with a preferred method being crossflow filtration. Concentration to a range of about 10 to 50% solids on a weight/volume basis is preferred. During concentration, the broth may be heated to a range of 50 to 70° C. to improve evaporation or filtration rate.

The broth is then adjusted to a pH greater than about 10, preferably between about 10 and about 11, using an appropriate basifying agent such as, for example, $Na_2CO_3$, $K_2CO_3$, KOH, NaOH, or a combination thereof. Depending on the degree of water removal in the concentration step, dilution of the concentrate with water or a water-miscible solvent may be necessary to facilitate agitation during the pH adjustment. Further, a substantially water-miscible solvent is added to the pH-adjusted concentrate in an amount sufficient to solubilize natamycin. Suitable water-miscible solvents include, for example, ethanol, propanol, isopropanol, acetone, tetrahydrofuran and combinations of the foregoing. Of these, isopropanol is preferred. Typically, one to two volumes of isopropanol is required per volume of concentrate.

Although the solubility of natamycin is low in either water or isopropanol ("Solubility of Antibiotics in Twenty-Six Solvents," Journal of the Association of Official Analytical Chemists, vol. 50, no. 2, 1967), it is soluble at 40 to 120 g/λ or more in the solvent mixture at elevated pH. Although the literature reports that natamycin is unstable at alkaline pH (H. Brik in "Analytical Profiles of Drug Substances"), in fact it is reasonably stable under the conditions of the present invention. If desired, stability can be further improved through addition of antioxidants such as ascorbic acid, erythorbic acid, BHA and BHT, at levels up to about 0.2 weight percent of the natamycin activity. Under the conditions of low pH recovery processes such as that disclosed in WO 92/10580, natamycin is susceptible to rapid activity loss and to the formation of natamycin analogs which are not readily separated from natamycin.

Inactive broth solids are removed from the natamycin solution by any of several methods such as depth filtration, crossflow filtration, or centrifugation. If desired, the solids may be washed, for example with 40 to 60% aqueous isopropanol, to extract residual natamycin activity and improve recovery yield. Crossflow filtration is a preferred method for removal of broth solids. Crossflow filtration, as defined by J. M. Walker and M. Cox in "The Language of Biotechnology" (American Chemical Society, Washington, D.C., 1988) is "an operating regime for a filtering device in which the main fluid flow is parallel to the filter, such that the fluid passes through the filter perpendicular to the main flow. This regime minimizes the buildup of filter cake and also the consequential reduction in filtration rate. It allows rapid filtration without the need for filter aids or flocculants." In the process claimed herein, crossflow filtration gives rapid filtration rates and high final solids concentrations without addition of filter aids. The ceramic filter elements which are used allow high crossflow rates, imparting an effective sweep of the filtration surfaces. They can be used at high temperatures, allowing further flux enhancement. Their stability to harsh pH and temperature conditions facilitates frequent cleaning, and they can be backpulsed during operation to minimize plugging.

The pH of the product-rich solution is then adjusted with a suitable acid such as hydrochloric acid to effect precipitation of natamycin. The choice of acid is not critical; for economy and simplicity, hydrochloric acid is preferred. The precipitated natamycin crystals are then isolated by an appropriate method such as, for example, depth filtration, crossflow filtration or centrifugation. This can be followed by further known purification steps, for example, washing with a water-isopropanol mixture followed by drying. Isolation of natamycin by centrifugation or crossflow filtration requires that the filtration mother liquor be displaced with a wash of similar solvent composition to avoid precipitating water-insoluble impurities. The dry product typically has a purity of at least 94% on an anhydrous basis. Recovery yields of 40–70% are typical. Crossflow filtration, as defined above, is a preferred method for isolation of natamycin, giving rapid removal of the mother liquor and wash liquid. The product in this case is a concentrated crystal slurry which can be converted to a dry solid by any of a number of methods, for example, evaporation or spray drying.

In crystalline form, natamycin is temperature stable (H. A. Morris, et al., *Cultured Dairy Products Journal*, p 23, (August 1978)). Sustained drying temperatures of 70° C. are acceptable as long as the product moisture is not driven below about 6%. Natamycin normally exists as a trihydrate. Anhydrous natamycin is less stable than the hydrate, so excessive drying adversely affects product purity.

Dry product purities of 94 to 99% (calculated on an anhydrous basis) and recovery yields of 40 to 70% are typically achieved through the inventive recovery process.

EXAMPLES

Example 1

On a rotary evaporator, 1027 ml of fermentation broth with a natamycin concentration of 10.5 g/λ was concentrated to 500 ml. The pH was adjusted to 10.5 with 10 M sodium hydroxide, and 500 ml of isopropanol was added. The mixture was stirred for about two hours, then centrifuged. The clear dark natamycin-rich solution was decanted, adjusted to pH 6.5–7.5 with 12 M hydrochloric acid, and allowed to crystallize for several hours. Natamycin crystals were isolated by centrifugation, transferred to a filter funnel with 40 ml of 1:1 water-isopropanol, filtered, washed with three 20 ml portions of 1:1 water-isopropanol, and dried to constant weight at 35° C. in a vacuum oven, yielding 8 g of natamycin solids which were 96.2% pure on an anhydrous basis. The yield from broth was 69%.

Example 2

A 10.2 liter portion of fermentation broth concentrate with a natamycin concentration of 134 g/λ was adjusted to pH 10.6 by addition of 1100 g of sodium carbonate, 140 ml of 50% sodium hydroxide solution, and sufficient water (1.3 λ) to allow the heavy concentrate to be mixed during pH adjustment. To the resulting slurry, 6 kg of isopropanol containing 6 g of BHA was added, and the mixture was stirred to dissolve natamycin. Broth solids were removed by crossflow filtration at 25–30° C. During this operation, as the retained slurry of broth solids thickened, 10 λ of 1:1 isopropanol-water was added to wash out residual natamycin. The filtrate was adjusted to pH 6.6 with 5 M hydrochloric acid, and natamycin was allowed to crystallize for 1–2 hours. Natamycin was isolated by filtration on a Buchner funnel, washed with about 500 ml of 40:60 isopropanol-water followed by about 500 ml of water, and dried in a laboratory hood to 550 g of natamycin solids which were greater than 97% pure on an anhydrous basis. The yield from broth concentrate was about 40%.

Example 3

A 9600-gallon volume of fermentation broth containing 1.06% natamycin was concentrated to a volume of 535 gallons by crossflow filtration at 55–60° C. During this operation, as the retained slurry thickened, 915 gallons of water was added as a wash. When the retained washed broth concentrate was no longer filterable, it was adjusted to pH 10.6 with sodium carbonate and sodium hydroxide, 8000 kg of isopropanol was added to dissolve natamycin, and one pound of sodium erythorbate was added to protect against oxidation. Broth solids were removed by crossflow filtration at 23–28° C. During this operation, as the retained slurry of broth solids thickened, 1625 gallons of 1:1 isopropanol-water was added to wash out residual natamycin. The filtrate containing natamycin was adjusted to pH 6.5 with hydrochloric acid. Natamycin was allowed to crystallize for 1–2 hours, then isolated by filtration, washed with water and dried, giving about 240 kg of natamycin which was 98% pure on an anhydrous basis. The yield was about 60%.

We claim:

1. A process for recovering natamycin from fermentation broth containing natamycin comprising the steps:

a) adjusting the pH of said broth to greater than about 10 and adding an amount of a substantially water-miscible solvent sufficient to dissolve the natamycin in said broth;

b) removing insoluble solids from said pH-adjusted broth;

c) lowering the pH of said broth to a level sufficient to precipitate the natamycin; and d) removing the natamycin from said broth.

2. A process according to claim 1 wherein said water-miscible solvent is selected from the group consisting of ethanol, propanol, isopropanol, acetone, tetrahydrofuran and combinations thereof.

3. A process according to claim 2 wherein said water-miscible solvent is isopropanol.

4. A process according to claim 1 wherein, in step a), the pH of said broth is adjusted to between 10 and 11.

5. A process according to claim 3 wherein, in step a), the pH of said broth is adjusted to between 10 and 11.

6. A process according to claim 1 wherein, in step c), the pH of said broth is lowered to between 5.5 and 7.5.

7. A process according to claim 5 wherein, in step c), the pH of said broth is lowered to between 5.5 and 7.5.

8. A process according to claim 1 wherein step b) utilizes crossflow filtration.

9. A process according to claim 7 wherein step b) utilizes crossflow filtration.

10. A process according to claim 1 further comprising the preliminary step of concentrating said broth.

11. A process according to claim 10 wherein said broth is concentrated to a concentration of 10 to 50% solids on a weight/volume basis.

12. A process according to claim 10 wherein said preliminary step utilizes crossflow filtration.

* * * * *